United States Patent [19]

Spector

[11] Patent Number: 4,556,539
[45] Date of Patent: * Dec. 3, 1985

[54] DISC-PLAYING AROMA GENERATOR

[76] Inventor: Donald Spector, 380 Mountain Rd., Union City, N.J. 07087

[*] Notice: The portion of the term of this patent subsequent to Aug. 24, 1999 has been disclaimed.

[21] Appl. No.: 477,353

[22] Filed: Mar. 21, 1983

Related U.S. Application Data

[63] Continuation-in-part of Ser. No. 412,080, Aug. 27, 1982.

[51] Int. Cl.$^4$ ................................................ A61L 9/03
[52] U.S. Cl. ..................................... 422/125; 239/56; 239/57; 422/4; 422/5
[58] Field of Search .................... 422/4, 116, 124, 125, 422/305, 306; 239/56, 57

[56] References Cited

U.S. PATENT DOCUMENTS

| | | | |
|---|---|---|---|
| 595,432 | 12/1897 | Bell | 422/125 |
| 1,389,074 | 8/1921 | Sharp | 422/305 |
| 1,920,599 | 8/1933 | Schuh | 422/306 |
| 2,501,496 | 3/1950 | Cartwright | 422/4 |
| 2,614,820 | 10/1952 | Boydjieff | 422/116 X |
| 2,931,880 | 4/1960 | Yaffe | 422/4 X |
| 2,942,090 | 6/1960 | Diehl | 422/125 X |
| 3,006,042 | 10/1961 | Calandra | 422/306 X |
| 3,551,092 | 12/1970 | Masson | 422/125 |
| 3,685,734 | 8/1972 | Pacioreck et al. | 239/56 |
| 3,820,308 | 6/1974 | Onuki | 422/4 X |
| 3,823,873 | 7/1974 | Miller et al. | 239/56 X |
| 3,872,280 | 3/1975 | Van Dalen | 422/125 X |
| 3,908,905 | 9/1975 | Von Philipp et al. | 239/57 X |
| 3,959,642 | 5/1976 | Torro | 422/125 X |
| 3,990,848 | 11/1976 | Corris | 422/116 X |
| 3,993,444 | 11/1976 | Brown | 422/116 |
| 4,078,891 | 3/1978 | Madjar | 422/116 |
| 4,102,656 | 7/1978 | Koritz | 422/124 X |
| 4,145,001 | 3/1979 | Weyenberg et al. | 239/56 |
| 4,166,087 | 8/1979 | Cline et al. | 422/116 X |
| 4,214,146 | 7/1980 | Schimanski | 422/306 X |
| 4,229,415 | 10/1980 | Bryson | 422/116 X |
| 4,306,892 | 12/1981 | Atalla et al. | 422/4 X |
| 4,346,059 | 8/1982 | Spector | 422/125 |
| 4,367,203 | 1/1983 | Landsberger | 422/306 X |
| 4,374,571 | 2/1983 | Hirvela | 239/56 X |

FOREIGN PATENT DOCUMENTS 2062199 5/1981 United Kingdom ................ 422/125

Primary Examiner—Barry S. Richman
Assistant Examiner—Brion P. Heaney
Attorney, Agent, or Firm—Michael Ebert

[57] ABSTRACT

A disc-playing aroma generator whose appearance and function are analogous to those of a phono disc record player, the user when playing a selected aromatic disc enjoying an olfactory rather than an auditory experience. Each aromatic disc houses a supply of a liquid fragrance whereby when the disc is inserted in the player, an aromatic vapor is then discharged into the atmosphere. The disc is formed by a circular sheet of absorbent material impregnated with the liquid fragrance and sandwiched between a pair of annular plastic films which are peripherally joined to create a central zone exposing the impregnated sheet. In the player, heated air under positive pressure is forced through the central zone to volatilize the liquid to produce a vapor which is discharged through vents in the casing of the player. The aromatic disc is packaged in a transparent sleeve having circular spindle labels on both sides thereof which overlie the central zone to impart thereto the appearance of a conventional phono record and serving to identify the fragrance.

4 Claims, 9 Drawing Figures

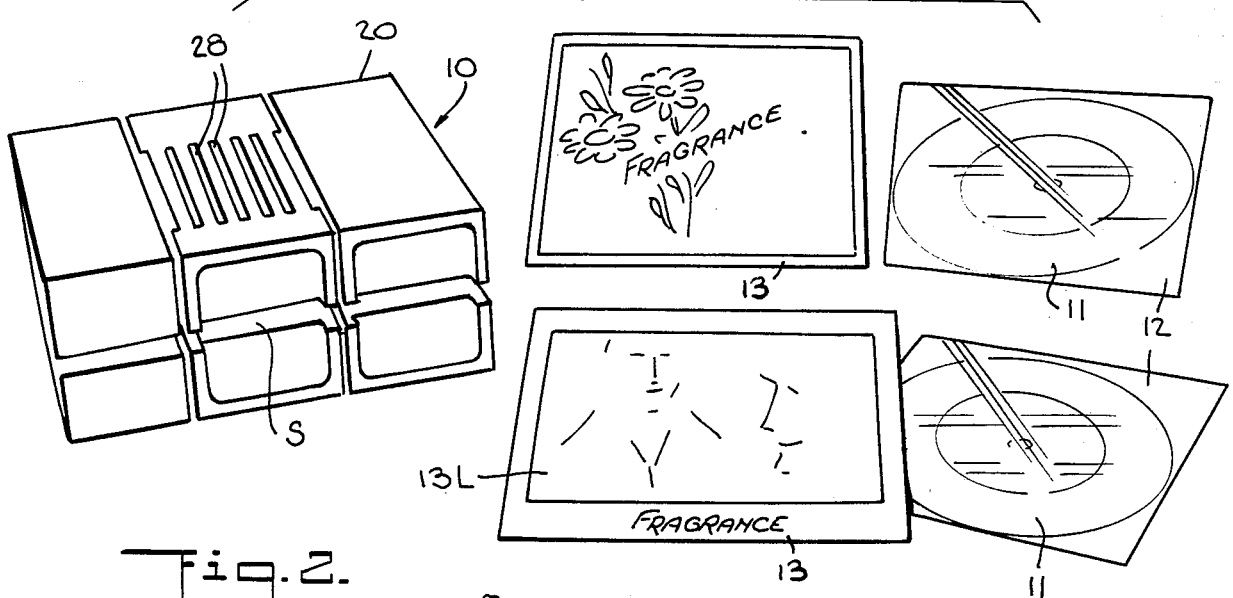
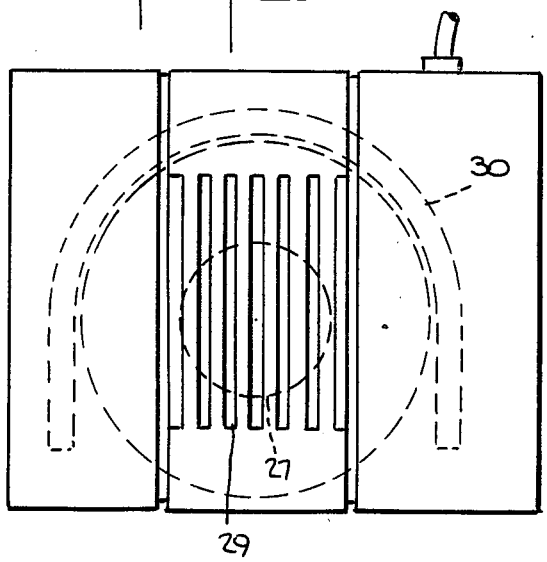
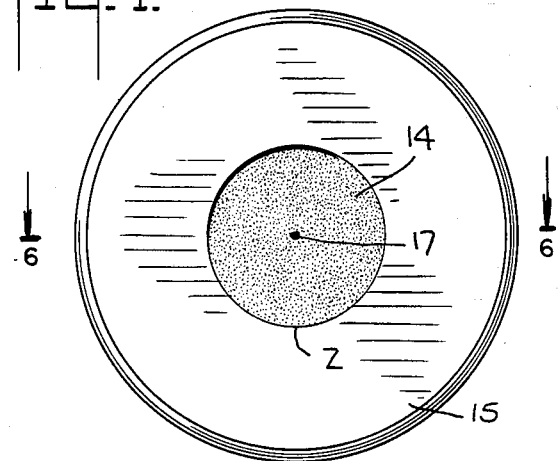
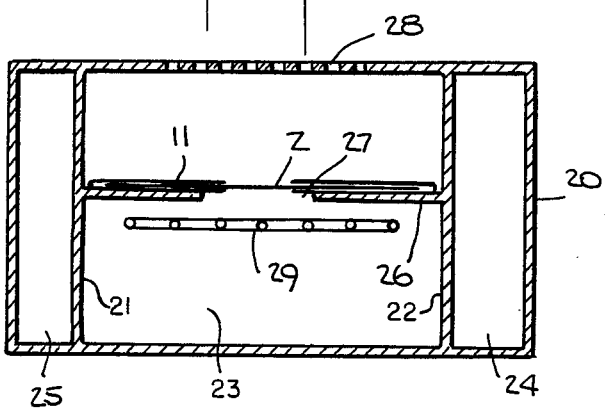
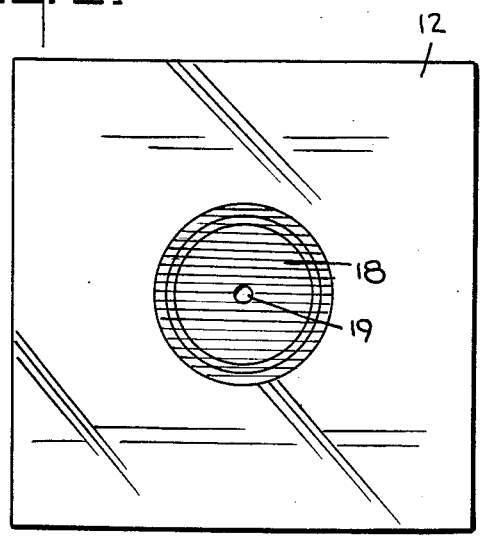

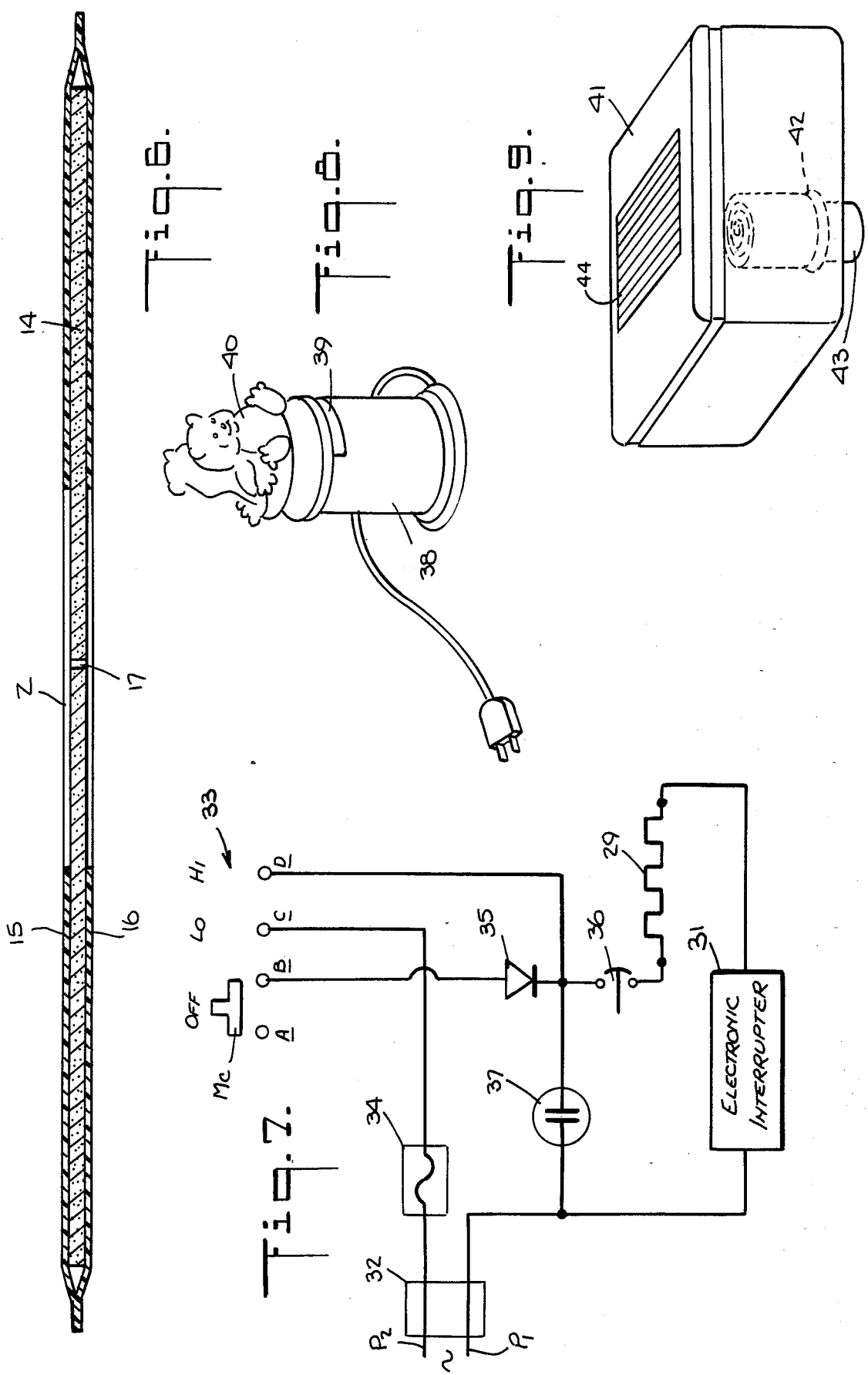

4,556,539

DISC-PLAYING AROMA GENERATOR

BACKGROUND OF INVENTION

Field of Invention

This invention relates generally to aroma generators, and more particularly to a disc-playing aroma generator whose appearance and function are analogous to those of a phono record player, each disc to be played having a supply of liquid fragrance, whereby when an aromatic disc is inserted in the player and the player is activated, an aromatic vapor is then discharged into the atmosphere.

As used herein, the term "aroma" is not limited to pleasant or savory smells, but encompasses scents that function as insecticides, air fresheners, deodorants or any other odor that acts to condition, modify or otherwise charge the atmosphere. Hence, in a disc-playing aroma generating unit, in accordance with the invention, one has a choice of discs to play, the selection depending on the atmospheric effect to be created.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents the ingredients are combined with alcohol.

Various types of spray devices or dispensers are known for emitting aromas. Thus the patent to Dearling, U.S. Pat. No. 4,084,732, disclosed a dispenser for wafting into the atmosphere an insecticide, a pleasant smelling scent or any other aroma, this being accomplished by means of a pressurized container. When the actuating button of this container is pressed, a dispersant is released onto an absorbent material, the absorbent dispersant permeating the atmosphere.

The difficulty with an aroma dispenser which functions to spray a charge of liquid onto a pad of absorbent material is that at ambient temperature the liquid, even when it has a high alcohol content, is slow to volatilize; hence the resultant odor, though of sufficient strength in the confines of an automotive interior, may lack adequate intensity in those environments which are relatively open, such as the living room or bedroom of a home.

It is known to promote vaporization of aroma-producing liquids by means of an electric bulb which also generates heat. Thus the Eisner U.S. Pat. No. 2,372,371 shows a pad saturated with a deodorant held in a small container mounted directly on the bulb. Similar bulb arrangements to promote vaporization are disclosed in the Gudeman U.S. Pat. No. 1,403,548; the Fusay et al. U.S. Pat. No. 2,557,501; and the Schlesinger U.S. Pat. No. 2,435,756.

In my prior U.S. Pat. No. 4,346,059 there is disclosed an aroma generator in which a pad of porous material impregnated with an aroma-producing liquid is disposed under a vent in a substantially enclosed housing. An electrical heating element placed in the housing acts to heat and expand the air confined therein to create a positive air pressure producing a pressure differential between the heated air and the atmosphere above the vent, as a consequence of which the heated air is driven through the pad to rapidly volatilize the liquid and exude an aromatic vapor though the vent into the atmosphere.

My patented unit is more efficient than those which use heat in conjunction with pads saturated with an aroma producing liquid, for the positive air pressure created in my unit results in a far more effective aroma generator.

The olfactory organs are chemi-receptors which are stimulated by minute quantities of gases or vapors in air as low as one part in one million of air. The olfactory cells are connected with the brain by the fibers of the olfactory nerves. The perception of smell by an individual's brain is such, that if a given smell persists, the individual ceases to be aware of the smell, for he makes an accommodation to the odor which is then treated as the prevailing environment. Thus one who first enters a hospital environment becomes immediately conscious of an antiseptic odor, but his sensitivity thereto diminishes and virtually disappears if the individual remains in this environment. When, however, he leaves the hospital and is exposed to the outside atmosphere, he quickly senses this change.

Thus the operation of the olfactory system is such that it is highy responsive to a change in the nature or level of an aroma but is desensitized when the prevailing odor attains a steady state condition. Hence in a room having an aroma generator of the type disclosed in my U.S. Pat. No. 4,346,059 in which an aromatic vapor is continuously exuded, persons in the room subjected to the vapor cease in time to become aware of the aroma, and the generator, even though it continues to operate, serves no useful purpose.

In my related copending application Ser. No. 412,080, there is disclosed an aroma generator unit which includes a hollow case whose upper wall has a vent therein and whose side wall has a slot to receive a replaceable cartridge provided with a porous mat impregnated with an aroma-producing liquid. When fully inserted, the cartridge is disposed below the vent and serves to define an air-confined chamber within the case.

Disposed in the chamber is an electrical heater which is periodically energized by power pulses separated by inactive intervals. The pulse-actuated heater acts to heat and expand the confined air to produce a positive pressure in the chamber, forcing the heated air through the mat to volatilize the liquid and to produce bursts of aromatic vapor which are discharged into the atmosphere through the vent. The non-aromatic intervals have a duration sufficient to permit recovery of the olfactory response of those exposed to the vapor to avoid desensitizing the response.

SUMMARY OF INVENTION

The main object of this invention is to provide a disc-playing aroma generator whose appearance and function are analogous to those of a conventional phono record player, each aromatic disc to be played housing a supply of a particular liquid fragrance whereby when the disc is inserted in the player, an aromatic vapor is then discharged into the atmosphere.

In a conventional phono disc record player, the user chooses from his library of records, a recording he wishes to hear and then inserts the selected disc in a player which reproduces the record, thereby filling the room with sound. A significant feature of the present invention is that in order to fill the room with a pleasing or mood-modifying aroma, the user selects from his library of aromatic discs a disc having the desired aroma which he then inserts in the player.

Thus, as between an aromatic disc player and a conventional phone disc record player, the distinction lies in the nature of the sensory experience—the former creating an olfactory and the latter an auditory sensation. However, to carry the analogy still further, with a disc-playing aroma generator in accordance with the invention, one may acquire jacketed aromatic discs in the same manner as one purchases phono disc records, the purchaser selecting discs whose aromas represent his personal preference.

More particularly, an object of this invention is to provide an aromatic disc player which functions to freshen or scent the room or environment in which the unit is placed, the unit acting to periodically discharge into this environment bursts of aromatic vapor, the non-aromatic intervals therebetween having a duration sufficient to avoid desensitizing the olfactory response of the individuals exposed to the vapor.

Also an object of the invention is to provide an aromatic disc and sleeve assembly which has the appearance of a conventional phono disc record.

Still another object of the invention is to provide a unit of the above type which operates efficiently and reliably and which may be manufactured at low cost.

Briefly stated, these objects are attained in a discplaying aroma generator whose appearance and function are analogous to those of a phono disc record player, the user when playing a selected aromatic disc enjoying an olfactory rather than an auditory experience. Each aromatic disc houses a supply of a liquid fragrance whereby when the disc is inserted in the player, an aromatic vapor is then discharged into the atmosphere. The disc is formed by a circular sheet of absorbent material impregnated with the liquid fragrance and sandwiched between a pair of annular plastic films which are peripherally joined to create a central zone exposing the impregnated sheet. In the player, heated air under positive pressure is forced through the central zone to volatilize the liquid to produce a vapor which is discharged through vents in the casing of the player. The aromatic disc is packaged in a transparent sleeve having circular spindle labels on both sides thereof which overlie the central zone to impart thereto the appearance of a conventional phono record and serving to identify the fragrance.

OUTLINE OF DRAWINGS

For a better understanding of the invention as well as other objects and further features thereof, reference is made to the following detailed description to be read in conjunction with the accompanying drawings, wherein:

FIG. 1 illustrates, in perspective, a disc-playing aroma generator in accordance with the invention constituted by a player and two aromatic disc and sleeve assemblies and their associated outer jackets;

FIG. 2 is a section taken in a horizontal plane extending through the player to show the relationship of the disc inserted therein to the heater contained in the assembly;

FIG. 3 is a section taken in a vertical plane extending through the player;

FIG. 4 is a plan view of an aromatic disc;

FIG. 5 shows the sleeve for the disc;

FIG. 6 is a section taken in the plane indicated by lines 6—6 in FIG. 4;

FIG. 7 is the schematic circuit diagram of the player;

FIG. 8 illustrates, in perspective an aromatic disc player intended for a child;

FIG. 9 illustrates, in perspective an aromatic disc player intended for the interior of an automobile.

DESCRIPTION OF INVENTION

1. First Embodiment:

Referring now to FIG. 1, there is shown a disc-playing aroma generator in accordance with the invention consisting of a player 10 whose appearance resembles that of a conventional phono disc record player, and two aromatic discs 11 therefor. Each disc is packaged in a transparent sleeve 12 to provide a sealed assembly which is normally stored in a jacket 13. This jacket is of rigid cardboard or other suitable material comparable to that used for conventional records.

The face of the jacket has a large rectangular label 13L thereon containing a photograph or other graphic material appropriate to the identified disc fragrance. Thus if the fragrance is that of a particular flower, that flower may be photographed. If on the other hand, the fragrance is intended to create a romantic mood and has no relationship to an existing flower or other odoriferous object, the photograph may be suggestive of romance. Thus the jacket gives a potential purchaser an impression of the nature of the disc aroma and its environmental characteristics.

While only two aromatic discs are shown, in practice, a library of many discs having different aromas may be provided so that the user can select from a broad spectrum of fragrances.

Each disc 11 as shown in FIGS. 4 and 6 is composed of a circular sheet 14 of absorbent material having good wicking properties such as blotting paper, non-woven fabric or flexible open cell foam plastic material, the sheet being sandwiched between a pair of annular films 15 and 16 of black synthetic plastic material formed of polyester such as Mylar, PVC or other suitable plastic which is impervious to and non-reactive with the liquid fragrance which impregnates the sheet 14.

The films 15 and 16 are joined together at their periphery so that sheet 14 is exposed only in the central circular zone Z defined by the annular film. In practice, a small spindle hole 17 may be bored in the center of the sheet to relieve an excessive air pressure build-up in the player. The liquid fragrance is added to the absorbent sheet after the disc is assembled through open zone Z, the liquid being dispersed throughout the entire sheet because of its wicking properties. Thus sheet 14 represents a supply of liquid fragrance.

Disc 11 is packaged in transparent plastic sleeve 12 which shown separately in FIG. 5 is provided on either side with circular labels 18 having simulated spindle holes 19. The dimensions of the sleeve relative to the disc are such that when the aromatic disc is inserted in the sleeve, the labels then overlie zone Z on the disc so that the labels appear to cover both sides of this zone. Thus the disc and the sleeve form an assembly whose aromatic disc has spindle labels, just like a record disc.

Sleeve 12, is a square envelope having an open side to permit insertion of the disc. The open side is sealed or is provided with a pressure-operated locking strip for this purpose to prevent the loss of fragrance from the disc by evaporation during prolonged storage. By using a thermoplastic film material such as PVC for the sleeve, sealing may be effected ultrasonically or by a heated pressure bar or wheel. Alternatively, the sleeve may be provided with a flap at the open side which is closed after disc insertion.

In a conventional phono disc record, the recording on each side is a spiral track running from the periphery of the disc to central zone, this zone being covered by a label which identifies the recording. In the present arrangement, the labels on the sleeves serve to identify the fragrance contained in the disc.

Referring now to FIGS. 2 and 3 which illustrate the internal structure of player 10, it will be seen that the boxlike casing 20, having side walls, a bottom wall, a top wall, and a front wall and which may be fabricated of rigid plastic material of good structural strength, is divided by vertical partitions 21 and 22 into a central chamber 23 flanked by side chambers 24 and 25. On the front wall of the case as shown in FIG. 1 there is a slot S which admits an aromatic disc 11 into central chamber 23. The side chambers are occupied by the circuit components associated with the heater element in the central chamber, which components are shown in FIG. 7.

The disc 11 inserted in the slot rests on a ledge 26 having a port 27 therein which registers with the open zone Z of the disc. An arcuate ridge 30 on the ledge is adapted to retain the inserted disc at its proper position in the chamber. The top wall of case 20 at the central chamber 23 is provided with vents 28 which are positioned above the inserted disc. These vents also function to simulate the loud-speaker vents in a conventional record player. Disposed below ledge 26 is an electrical heating element 29, which when activated heats the surrounding air.

2. Operation:

When heater 29 is energized, it acts to heat the air in the confined region within a heating chamber, the heating chamber being that portion of the central chamber 23 located below the inserted disc 11. Because this heated air is confined, the resultant expansion of the air produces a positive pressure in this region, causing the heated air to force its way through open zone Z by way of the liquid impregnated sheet 14, thereby volatilizing the liquid fragrance to generate an aromatic vapor which is discharged into the atmosphere through vent 28.

The heater is preferably periodically energized so that as to produce periodic bursts of vapor separated by non-aromatic intervals having a duration sufficient to permit recovery of the olfactory response of those exposed to the vapors to avoid desensitizing this response.

The operating circuit for this purpose is shown in FIG. 7, where it will be seen that one end terminal of heater 29 is connected through an electronic interrupter 31 to one prong $P_1$ of a plug 32. This plug is insertable into a standard a-c power line outlet (110 v). A selector switch 33 is provided having fixed contacts A, B, C and D and a movable bridging connector MC. The connector is shiftable from an "Off" position at which it bridges contacts A and B, to a "Lo" position at which it bridges contacts B and C, and finally to a "Hi" position at which it bridges contacts C and D.

The other prong $P_2$ of line plug 32 is connected to contact C through a temperature sensitive cut-off device 34 which is installed in the central chamber and serves to cut-off power in the event the temperature therein rises above a predetermined safety limit. Contact B is connected through a diode 35 to the opposite end terminal of heater element 29, a thermostatic switch 36 being interposed between diode 35 and this terminal. Contact D is connected to the junction of diode 35 and thermostatic switch 36, pilot light 37 is connected between this junction and prong $P_1$, this light going on only when the heater is energized.

Thus when movable connector MC is in its "Off" position, no power is supplied to heater element 29. When it occupies its "Lo" position, power is supplied to the heater element through diode 35 which half-wave rectifies the a-c power so that the heater is then energized by half cycles of the power and therefore operates with reduced power to generate an aromatic vapor at a relatively low rate. Thus when the unit is installed in a small room, it may be desirable to operate it at the "Lo" position.

When movable contact MC is at its "Hi" position, full power is applied to heater 29 to produce an aromatic vapor at a rapid rate. In both the "Lo" and "Hi" mode, thermostatic switch 36 cuts off when the chamber temperature exceeds a predetermined level, thereby maintaining the selected rate of vapor discharge. And in both modes, interrupter 31 acts to periodically switch on the power supplied to the heater to provide the desired pulsatory pattern of vapor-on and vapor-off to avoid desensitizing the response of those subjected to the aromatic vapor. In practice, one may dispense with this interrupter.

3. Other Embodiments:

As shown in FIG. 8, instead of having an aroma-generator player which resembles a conventional phono record player, it may take the form of a cylindrical hollow pedestal 38 having a slot 39 therein to receive an aromatic disc 11, the pedestal housing the required heater and operating circuit. Mounted on the pedestal is a hollow animal-like figure 40 having holes therein to provide the necessary vents through which the aromatic vapor is discharged.

This toy-like player is suitable for young children who can then play, as it were, their favorite odors. It can, of course, also be used as an educational toy to teach children the distinctions between the smells of different fruits and flowers. The embodiment has play value, for children may then be asked to identify the fragrance being discharged, and a competition may be set up to give a prize to the child who makes the greatest number of correct identifications.

In the aroma generator shown in FIG. 9, the case 41 of the player is provided with a base port 42 adapted to receive a cylindrical cigarette lighter 43 of the type conventionally used in automobiles. This lighter is provided with a spiralled heating coil which is energized by the auto battery when the lighter is pushed into a dashboard power socket, the lighter being ejected automatically when the heater coil is red hot. The player is also provided with a slot to receive an aromatic disc.

This aroma generator may be mounted under the dashboard in the vehicle and activated simply by first activating the lighter in its power socket and then transferring the lighter to the player as shown in FIG. 9. While this source of heat is not in pulsatory form and of relatively short duration, it is sufficient to cause a discharge of aromatic vapor through vent 44 in the case 41 of the player in an amount which suffuses the interior of the vehicle and thereby renders its environment more pleasing or stimulating. Also for this purpose, use may be made of a de-odorizer rather than a fragrant liquid.

Thus in practice, the configuration of the player need not be that of a conventional record player but may take many other ornamental or fanciful forms as long as the player is provided with a source of heat in a confined region to produce a positive air pressure, forcing the heated air through the open zone Z of the aromatic disc.

While there has been shown and described preferred embodiments of disc-playing aroma generator, it will be appreciated that many changes and modifications may be made therein without, however, departing from the essential spirit thereof. Thus while the disc has been disclosed as including a pair of annular plastic films, in practice use is preferably made for this purpose of composite films formed by aluminum foil having a thin layer of black thermoplastic material coated on both sides thereof, thereby concealing the metal. The advantage of the composite film is that the aluminum foil not only stiffens disc 11 as to avoid floppiness, but it also functions as a heat sink and radiator to absorb and dissipate heat developed in the confined region, thereby preventing excessive heating thereof. Because of the thermoplastic layers, the composite films may be bonded together at their periphery in the same manner as pure plastic material.

I claim:

1. A disc-playing aroma generator kit comprising:
   A. a replaceable aromatic disc constituted by a circular sheet of absorbent material having good wicking properties impregnated with a liquid fragrance and sandwiched between a pair of annular films, the outer periphery of which extend beyond the outer periphery of said sheet, and which are impervious to said liquid fragrance, said annular films are joined at their outer periphery to provide a liquid impermeable seal there at and to create a central zone exposing the central region of said sheet, whereby said disc simulates the appearance of a conventional phono disc record;
   B. a disc player having a case provided with a vented top wall, side walls, a bottom wall, a front wall having a disc receiving slot therein, a horizontal ledge intermediate to said bottom wall and said vented top wall and in alignment with said slot, said ledge having an opening therein which registers with said exposed central region of a received disc, said ledge and a received disc dividing the case to form a heating chamber therebelow so that when a disc is received in said slot a confined air region is created in said heating chamber, and a heater disposed in said heating chamber to heat and expand the air therein whereby the resultant positive air pressure forces the heated air through the central region of the sheet to volatilize the liquid fragrance impregnant therein and to produce an aromatic vapor that is discharged into the atmosphere through said vented top wall, the liquid fragrance volatilized from said central region being replenished by liquid fragrance wicked from the remaining region of said sheet surrounding the central region thereof which serves as a liquid reservoir.

2. An aroma generator kit as set forth in claim 1, wherein said player takes the form of a hollow pedestal which defines said case, said pedestal having a hollow figure mounted thereon provided with vents to permit discharge of the aromatic vapor.

3. An aroma generator kit as set forth in claim 1 wherein said annular films are formed of flexible black plastic film material.

4. An aroma generator kit as set forth in claim 3, wherein said annular films are formed of polyester.

* * * * *